United States Patent [19]

Kobayashi et al.

[11] Patent Number: 5,728,857
[45] Date of Patent: Mar. 17, 1998

[54] SILICON-CONTAINING PEROXYESTERS

[75] Inventors: Takashi Kobayashi; Tadashi Amano, both of Kamisu-machi; Hideshi Kurihara, Yokohama; Tomohisa Suzuki, Urawa; Toshio Shinohara, Takasaki; Tohru Nishikawa, Taketoyo-machi, all of Japan

[73] Assignee: Shin-Etsu Chemical Co., Ltd., Tokyo, Japan

[21] Appl. No.: 813,588

[22] Filed: Mar. 7, 1997

[30] Foreign Application Priority Data

Mar. 26, 1996 [JP] Japan .................................. 8-096084

[51] Int. Cl.$^6$ ............................................. C07F 7/08
[52] U.S. Cl. ............................. 556/437; 556/436; 554/77
[58] Field of Search ............................. 556/437, 436; 554/77

[56] References Cited

U.S. PATENT DOCUMENTS 5,374,759  12/1994  Imperante et al. ............... 556/437

Primary Examiner—Paul F. Shaver
Attorney, Agent, or Firm—Oblon, Spivak, McClelland, Maier & Neustadt, P.C.

[57] ABSTRACT

Silicon-containing peroxyester compounds, for example, represented by the following formula:

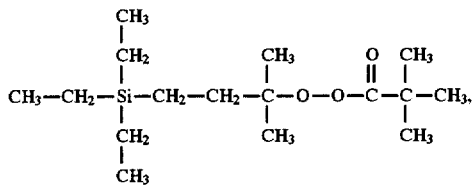

useful as a polymerization initiator, which compounds can produce vinyl chloride polymers having a high quality in a high yield and in a short reaction time.

2 Claims, No Drawings

SILICON-CONTAINING PEROXYESTERS

BACKGROUND OF THE INVENTION

1. Field of the Invention

The present invention relates to a novel silicon-containing peroxyester compound useful as an initiator for radical polymerization reaction of vinyl monomers.

2. Description of the Prior Art

In the production of vinyl polymers obtained by radical-polymerization of vinyl monomers such as vinyl chloride, vinylidene chloride, vinyl acetate, acrylonitrile, (meth) acrylic esters, and the like, there has been in recent years raised a demand for shortening reaction time in the polymerization process in order to improve productivity while maintaining quality of products.

The polymerization of these vinyl monomers is a radical reaction and is generally effected at a temperature of 30° to 70° C. using a radical polymerization initiator. In the polymerization of vinyl monomers, the pressure within a polymerization vessel drops at the latter stage of the polymerization as mentioned later. Therefore, the polymerization is stopped at the time when the internal pressure of the polymerization vessel dropped to a prescribed pressure. As the radical polymerization initiators to be used, there are conventionally used, if as an example the production of vinyl polymers is explained, for example, perester compounds such as 1) t-butyl peroxyneodecanoate, 2) cumyl peroxyneodecanoate, and the like; diacyl compounds such as 3) 3,5,5-trimethylhexanoyl peroxide, and the like; and carbonate compounds such as 4) di-2-ethylhexyl peroxydicarbonate, and the like. In the case of using the polymerization initiators of 1), 2) and 3), the pressure within the polymerization vessel begins to drop upon reaching the latter stage (that is, when the polymerization conversion becomes about 70% or more) of the polymerization. Since the reaction rate is rapidly reduced with the beginning of the pressure drop, there is the drawback that the polymerization time must be extended in order to attain a high yield. In the case of using the polymerization initiator of 4), vinyl chloride polymers can be obtained in a high yield by reacting for a relatively short time, but there is the drawback that the resulting vinyl chloride polymers are poor in initial discoloration and thus it is not proper to obtain vinyl chloride polymers having a high quality. As a solution of the problem that the reaction rate is rapidly reduced, there has been also proposed a method comprising adding an additional amount of the polymerization initiator before the pressure drop occurs. However, the use of this method results in the drawback that since fisheyes in products formed from the obtained vinyl chloride polymer increase and the amount of the residual polymerization initiator in the obtained vinyl chloride polymer increases, the initial discoloration of the obtained vinyl chloride polymer increases. For this reason, there is required a polymerization initiator, which is used in vinyl polymers, capable of producing vinyl chloride polymers having a high quality in a high yield and in a short reaction time.

The present invention relates to silicon-containing peroxyesters useful as a radical polymerization initiator for vinyl monomers, while an example using silicon-containing peroxyesters as a radical polymerization initiator is disclosed in Japanese Patent Pre-examination Publication (kokai) No. 60-199897. The Japanese Patent Pre-examination Publication (kokai) No. 60-199897 discloses, as a radical polymerization initiator for use in the ultraviolet-curing reaction of polyorganosiloxanes, a peroxyester compound represented by the following formula:

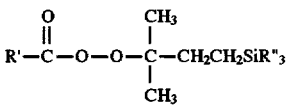

wherein R' is a substituted or unsubstituted phenyl group such as phenyl, o-chlorophenyl, m-chlorophenyl, p-chlorophenyl, 2,4-dichlorophenyl and p-isopropylphenyl groups, and the like; and R" are independently an alkyl group such as methyl, ethyl, propyl, butyl, amyl and hexyl groups, and the like, and a substituted or unsubstituted monovalent hydrocarbon group having 1 to 6 carbon atoms such as a phenyl group, and the like.

Since the above silicon-containing peroxyester has a 10-hour half-life period temperature of 80° C. or more in a benzene solution containing 0.1 mole of said peroxyester per liter of benzene, the polymerization yield can not be readily increased to a prescribed value when used in the polymerization carrying out at a temperature in the range of 30° to 70° C., even if the polymerization time is extended. Therefore, it is improper to use this silicon-containing peroxyester in order to improve productivity in the production of vinyl polymers.

SUMMARY OF THE INVENTION

Accordingly, the task of the present invention is to provide a novel silicon-containing peroxyester compound useful as a radical polymerization initiator, which compound enables to produce vinyl chloride polymers having a high quality in a high yield and in a short reaction time.

The present inventors have earnestly studied and, as a result, have found a silicon-containing peroxyester compound, which is capable of solving said task and is a novel compound useful as a radical polymerization initiator, represented by the general formula (1):

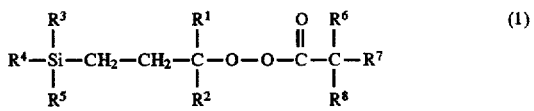

wherein $R^1$ and $R^2$ are the same or different and are a straight-chain alkyl group having 1 to 6 carbon atoms or a branched chain alkyl group having 3 to 6 carbon atoms; $R^3$, $R^4$ and $R^5$ are the same or different and are a straight-chain alkyl group having 1 to 6 carbon atoms, a branched chain alkyl group having 3 to 6 carbon atoms or an aryl group having 6 to 9 carbon atoms; and $R^6$, $R^7$ and $R^8$ are the same or different and are a straight-chain alkyl group having 1 to 9 carbon atoms, provided that the total number of the carbon atoms of $R^6$, $R^7$ and $R^8$ is 11 or less.

The silicon-containing peroxyester compound of the present invention is useful as a radical polymerization initiator for obtaining, for example, vinyl chloride polymers, and can produce vinyl chloride polymers having a high quality in a high yield and in a short reaction time, said polymers being capable of producing formed products especially low in initial discoloration.

DESCRIPTION OF THE PREFERRED EMBODIMENTS

The compound of the general formula (1) is hereinafter described.

In the general formula (1), $R^1$ and $R^2$ are the same or different from each other and represent a straight-chain alkyl group having 1 to 6 carbon atoms, that is, a methyl, ethyl, n-propyl, n-butyl, n-pentyl or n-hexyl group; or a branched chain alkyl group having 3 to 6 carbon atoms, for example, isopropyl, sec-butyl, isobutyl, tert-butyl, 1-methylbutyl, 2-methylbutyl, 3-methylbutyl, 1-methylpentyl, 2-methylpentyl and 3-methylpentyl groups. Among them, preferred are methyl and ethyl groups.

$R^3$, $R^4$ and $R^5$ are the same or different from each other and represent a straight-chain alkyl group having 1 to 6 carbon atoms, that is, a methyl, ethyl, n-propyl, n-butyl, n-pentyl or n-hexyl group; a branched chain alkyl group having 3 to 6 carbon atoms, for example, isopropyl, sec-butyl, isobutyl, tert-butyl, 1-methylbutyl, 2-methylbutyl, 3-methylbutyl, 1-methylpentyl, 2-methylpentyl and 3-methylpentyl groups; or an aryl group having 6 to 9 carbon atoms, for example, a phenyl group, and the like. Among them, preferred is a methyl, ethyl, n-propyl, isopropyl, sec-butyl, isobutyl, tert-butyl or phenyl group.

$R^6$, $R^7$ and $R^8$ are the same or different from each other and represent a straight-chain alkyl group having 1 to 9 carbon atoms, that is, a methyl, ethyl, n-propyl, n-butyl, n-pentyl, n-hexyl, n-heptyl, n-octyl or n-nonyl group, and are a group such that the total number of the carbon atoms of $R^6$, $R^7$ and $R^8$ is 11 or less. If the total number of the carbon atoms of $R^6$, $R^7$ and $R^8$ is more than 11, the viscosity of the resulting compound becomes too high and thus, for example, it is difficult to pump the compound under pressure into a polymerization vessel when supplied into the polymerization vessel, whereby it becomes inconvenient for handling. The total number of the carbon atoms of $R^6$, $R^7$ and $R^8$ is more preferably 3 to 8.

Specific examples of the silicon-containing peroxyester compound according to the present invention include:

1,1-dimethyl-3-(triethylsilyl)propyl peroxypivalate, 1,1-dimethyl-3-(triethylsilyl)propyl peroxyneoheptanoate, 1,1-dimethyl-3-(triethylsilyl)propyl peroxyneodecanoate, 1,1-dimethyl-3-(phenyldimethylsilyl)propyl peroxypivalate, 1,1-dimethyl-3-(phenyldimethylsilyl)propyl peroxyneoheptanoate, 1,1-dimethyl-3-(phenyldimethylsilyl)propyl peroxyneodecanoate, 1,1-dimethyl-3-(tert-butyldimethylsilyl)propyl peroxypivalate, 1,1-dimethyl-3-(tert-butyldimethylsilyl)propyl peroxyneoheptanoate, 1,1-dimethyl-3-(tert-butyldimethylsilyl)propyl peroxyneodecanoate, 1-ethyl-1-methyl-3-(trietylsilyl)propyl peroxypivalate, 1-ethyl-1-methyl-3-(trietylsilyl)propyl peroxyneoheptanoate, 1-ethyl-1-methyl-3-(trietylsilyl)propyl peroxyneodecanoate, 1,1-dimethyl-3-(triethylsilyl)propyl peroxyneotridecanoate, 1,1-dimethyl-3-(phenyldimethylsilyl)propyl peroxyneotridecanoate, 1,1-dimethyl-3-(tert-butyldimethylsilyl)propyl peroxyneotridecanoate, 1-ethyl-1-methyl-3-(triethylsilyl)propyl peroxyneotridecanoate, and the like.

Among these, as a radical polymerization initiator for vinyl monomers, particularly preferred are:

1,1-dimethyl-3-(triethylsilyl)propyl peroxypivalate, 1,1-dimethyl-3-(triethylsilyl)propyl peroxyneoheptanoate, 1,1-dimethyl-3-(triethylsilyl)propyl peroxyneodecanoate, 1,1-dimethyl-3-(triethylsilyl)propyl peroxyneotridecanoate, 1,1-dimethyl-3-(tert-butyldimethylsilyl)propyl peroxypivalate, 1,1-dimethyl-3-(tert-butyldimethylsilyl)propyl peroxyneoheptanoate, 1,1-dimethyl-3-(tert-butyldimethylsilyl)propyl peroxyneodecanoate, 1,1-dimethyl-3-(tert-butyldimethylsilyl)propyl peroxyneotridecanoate, 1-ethyl-1-methyl-3-(trietylsilyl)propyl peroxypivalate, 1-ethyl-1-methyl-3-(trietylsilyl)propyl peroxyneoheptanoate, and 1-ethyl-1-methyl-3-(trietylsilyl)propyl peroxyneodecanoate.

Among the compound above, more preferred are 1,1-dimethyl-3-(triethylsilyl)propyl peroxypivalate, 1,1-dimethyl-3-(triethylsilyl)propyl peroxyneoheptanoate, 1,1-dimethyl-3-(triethylsilyl)propyl peroxyneodecanoate, 1,1-dimethyl-3-(triethylsilyl)propyl peroxyneotridecanoate, 1,1-dimethyl-3-(tert-butyldimethylsilyl)propyl peroxypivalate, 1,1-dimethyl-3-(tert-butyldimethylsilyl)propyl peroxyneoheptanoate, 1,1-dimethyl-3-(tert-butyldimethylsilyl)propyl peroxyneodecanoate, 1,1-dimethyl-3-(tert-butyldimethylsilyl)propyl peroxyneotridecanoate.

Synthesis

The silicon-containing peroxyester compound of the general formula (1) is synthesized, for example, in accordance with the following manner. (I) Initially, a triorganosilane represented by the general formula (2):

wherein $R^3$, $R^4$ and $R^5$ are as defined above, and an allyl alcohol compound represented by the general formula (3):

wherein $R^1$ and $R^2$ are as defined above, are reacted in the presence of a hydrosilylation catalyst such as a platinum compound or the like to obtain a silicon-containing alcohol represented by the general formula (4):

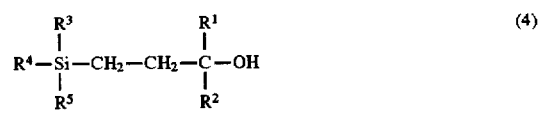

wherein $R^1$, $R^2$, $R^3$, $R^4$ and $R^5$ are as defined above.

The triorganosilane of the general formula (2), a reactant component, is exemplified by trimethylsilane, triethylsilane, tripropylsilane, tributylsilane, trihexylsilane, phenyldimethylsilane, diphenylmethylsilane, tert-butyldimethylsilane, di-tert-butylmethylsilane, ethyldimethylsilane, diethylmethylsilane, and the like.

The allyl alcohol compound of the general formula (3) is exemplified by 3-methyl-1-buten-3-ol, 3-methyl-1-penten-3-ol, 3-methyl-1-hexen-3-ol, 3,4,4-trimethyl-1-penten-3-ol, 3,5-dimethyl-1-hexen-3-ol, and the like.

Generally, the amount of the allyl alcohol compound of the general formula (3), is preferably 0.9 to 1.1 mole per mole of the triorganosilane of the general formula (2).

The hydrosilylation catalyst includes, for example, platinum catalysts such as platinum, chloroplatinic acid, and the like.

The above reaction is carried out at a temperature in the range of room temperature to 100° C. Further, the reaction may be effected in the absence of a solvent or, if necessary, may be effected in an organic solvent such as, for example, toluene, xylene, n-hexane, and the like. (II) Subsequently, treatment of the silicon-containing alcohol of the general formula (4) with an aqueous hydrogen peroxide and sulfuric acid, gives a silicon-containing hydroperoxide represented by the general formula (5):

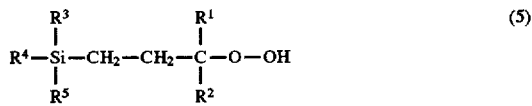

wherein $R^1$, $R^2$, $R^3$, $R^4$ and $R^5$ are as defined above. This reaction is an exothermic reaction and thus, it is proper to carry out the reaction at room temperature. (III) Then, by reacting the silicon-containing hydroperoxide of the general formula (5) with an acid chloride represented by the general formula (6):

wherein $R^6$, $R^7$ and $R^8$ are as defined above, in an organic solvent while maintaining the reaction temperature at 20° C. or less, there is obtained the intended silicon-containing peroxyester compound of the general formula (1).

The organic solvent to be used includes, for example, benzene, toluene, xylene, n-hexane, and the like.

Specific examples of the acid chloride of the general formula (6) include pivalic acid chloride, neoheptanoic acid chloride, neodecanoic acid chloride, neotridecanoic acid chloride, and the like.

Thus, the silicon-containing peroxyester compound of the general formula (1) is obtained in the form of a solution. By washing the reaction solution with water to be neutral and thereafter, for example, distilling off the solvent or recrystallizing the product from a suitable organic solvent, the silicon-containing peroxyester compound can be isolated.

Applicability

Since the silicon-containing peroxyester compound of the present invention has a 10-hour half-life period temperature in the range of 30° C. to 60° C. in a benzene solution containing 0.1 mole of said compound per liter of benzene, this peroxyester compound is suitable as a radical polymerization initiator for the polymerization of vinyl monomers of which polymerization temperature is in the range of 30° to 70° C. The types of the polymerization in this case are not particularly limited and include, for example, suspension polymerization, emulsion polymerization, bulk polymerization, and the like.

Vinyl monomers to be suitably used at a polymerization temperature in the range of about 30° to 70° C. are exemplified by vinyl chloride, vinylidene chloride, vinyl acetate, and the like.

The silicon-containing peroxyester compound of the general formula (1) is used as a polymerization initiator, and the amount of the compound having the general formula (1) to be added is 0.001 to 5 parts by weight, particularly 0.01 to 0.3 part by weight, per 100 parts by weight of the monomer to be charged.

As vinyl monomers used for obtaining vinyl polymers in the present invention, there can be enumerated vinyl chloride, vinylidene chloride, vinyl acetate, styrene, acrylonitrile, acrylic acid, methacrylic acid, acrylic acid esters, methacrylic acid esters, butadiene, chloroprene, and the like. They can be singly or in a combination of two or more thereof. Among them, the peroxyester compound of the invention is effective in polymerization of particularly vinyl chloride monomer, vinylidene chloride monomer, vinyl acetate monomer or a monomeric mixture comprised mainly of these monomers for producing vinyl chloride polymers, vinylidene chloride polymers or vinyl acetate polymers. The compound of the invention is especially effective in producing vinyl chloride polymers.

The vinyl chloride polymers herein include vinyl chloride homopolymer and besides copolymers of vinyl chloride with other vinyl monomers (generally, vinyl chloride being 50% by weight or more, preferably 70% by weight or more). The comonomers to be copolymerized with vinyl chloride are exemplified by α-olefins such as ethylene, propylene, 1-butene, 1-pentene, 1-hexene, 1-heptene, 1-octene, 1-nonene, 1-decene, 1-undecene, 1-dodecene, 1-tridecene, 1-tetradecene, and the like; maleic acid; vinyl esters such as vinyl acetate, and the like; vinyl ethers such as lauryl vinyl ether, isobutyl vinyl ether, and the like; maleic acid anhydride; vinylidene chloride; and the like.

The vinylidene chloride polymers include vinylidene chloride homoplymer and copolymers of vinylidene chloride with other vinyl monomers (generally, vinyl chloride being 50% by weight or more, preferably 70% by weight or more). The comonomers to be copolymerized with vinylidene chloride are exemplified by those except for vinylidene chloride per se among the above-mentioned comonomers.

The vinyl acetate polymers include vinyl acetate homoplymer and copolymers of vinyl acetate with other vinyl monomers (generally, vinyl acetate being 50% by weight or more, preferably 70% by weight or more). The comonomers to be copolymerized with vinyl acetate are exemplified by those except for vinyl acetate per se among the above-mentioned comonomers.

Further, suitable polymerization methods to be applied include suspension polymerization, emulsion polymerization, solution polymerization, bulk polymerization, and the like. Among them, however, particularly preferred is suspension polymerization.

As the suspension polymerization method, there can be applied known methods. The polymerization temperature is preferably 30° to 70° C., more preferably 40° to 65° C. Suspending agents to be used may be those conventionally used in general and include, for example, cellulose derivatives such as methyl cellulose, hydroxyethyl cellulose, hydroxypropyl cellulose, hydroxypropyl methyl cellulose, and the like; and water-soluble polymers such as a partially saponified water-soluble or oil-soluble polyvinyl alcohol, acrylic acid polymer, gelatin, and the like. They can be used singly or even as a combination of two or more thereof. Also together with the above-mentioned suspending agents, there can be used, for example, nonionic emulsifiers such as sorbitan monolaurate, sorbitan trilaurate, glycerin tristearate, ethylene oxide/propylene oxide block copolymer, and the like; anionic emulsifiers such as polyoxyethylene sorbitan monolaurate, polyoxyethylene glycerin oleate, sodium laurylsulfate, and the like; singly or in a combination of two or more thereof. The amount of the suspending agent to be used is added in the range of generally 0.02 to 0.2 part by weight per 100 parts by weight of the monomer to be charged.

Incidentally, it is also optional to add, if necessary, polymerization adjusters, chain transfer agents, pH adjusters, gelation adjusters, antistatic agents, crosslinking agents, fillers, polymer scale deposition preventive agents, and the like, which are used in polymerization methods for producing vinyl polymers.

EXAMPLES

The present invention will now be described below, with reference to Examples.

Example 1

Production of 1,1-dimethyl-3-(triethylsilyl)propyl peroxypivalate (1) Into a four-necked 500 mL-flask equipped with a stirring apparatus, a thermometer and a dropping funnel, 81.2 g (0.943 mole) of 3-methyl-1-buten-3-ol and 0.2 g of an n-butanol solution containing chloroplatinic acid at a concentration of 2 weight % were charged, and they were heated to 80° C. with stirring. From the dropping funnel, 109.6 g (0.943 mole) of triethylsilane was dropwise added into the four-necked flask. After the completion of the addition, they were heated and stirred for about 20 hours. Meanwhile, the proceeding of reaction was traced by gas chromatography analysis. At the stage when the proceeding of the reaction stopped, an additional mount of the above n-butanol solution containing chloroplatinic acid was added for the proceeding of the reaction. The reaction mixture was distilled under reduced pressure to obtain 154.9 g (0.765 mole) of 1,1-dimethyl-3-(triethylsilyl)propyl alcohol as a fraction at 105° C./14–16 torr.

(2) Subsequently, into a four-necked 100 mL-flask equipped with a stirring apparatus, a thermometer and a dropping funnel, 27.5 g (0.404 mole) of a 50 weight % aqueous solution of hydrogen peroxide was charged. Stirring was started, and 15.6 g (0.156 mole) of 98 weight %—concentrated sulfuric acid was dropwise added under stirring while maintaining the temperature at 20° C. or below by water-cooling to prepare a mixed acid. Then after raising the temperature to room temperature, 20.2 g (0.1 mole) of the 1,1-dimethyl-3-(triethylsilyl)propyl alcohol synthesized in (1) was slowly dropwise added with stirring. After the completion of the addition, stirring was continued for 8 hours and then the resulting reaction mixture was washed with pure water three times to remove hydrogen peroxide and sulfuric acid. From the mixture obtained, the reaction product was extracted with ethyl acetate. The extract liquid obtained was washed with water until the liquid became neutral. After the organic layer separated from the water layer was dehydrated with anhydrous sodium sulfate, the solvent was distilled off to obtain 13.8 g (0.063 mole) of 1,1-dimethyl-3-(triethylsilyl)propyl-1-hydroperoxide.

(3) Next, into a four-necked 50 mL-flask equipped with a stirring apparatus, a thermometer and a dropping funnel, 13.4 g (0.061 mole) of the 1,1-dimethyl-3-(triethylsilyl) propyl-1-hydroperoxide obtained in (2) was charged, and 19.6 g (0.147 mole) of a 30 weight % aqueous solution of potassium hydroxide was added and stirred for mixing. While maintaining the temperature at 0° C., 8.4 g (0.07 mole) of pivalic acid chloride was dropwise added with stirring, and stirring was further continued for 2 hours. Thereafter, the reaction liquid was washed with water until the liquid became neutral, followed by dehydrating with anhydrous sodium sulfate to the intended compound. The intended compound thus obtained was analyzed by the iodometry method. As a result, the yield was 11.9 g (0.039 mole) and 63.9% (mole yield based on acyl fluoride). Further, the obtained compound was analyzed for mass spectrum, IR spectrum and NMR spectrum. As a result, it was confirmed that the compound was 1,1-dimethyl-3-(triethylsilyl)propyl peroxypivalate. The 10-hour half-life period temperature of the obtained compound in a benzene solution containing 0.1 mole of the compound per liter of benzene was 49.4° C. and the amount of active oxygen was 5.29%. The results of the analyses are shown below.

Mass spectrometric analysis

Exact Mass: m/z 302.5299

$C_{16}O_3SiH_{34}$ 302.5297 (calculated)

NMR spectrometric analysis

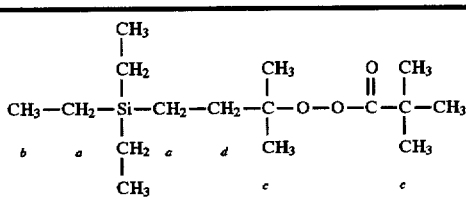

$^1$H-NMR (CDCl$_3$)

| | |
|---|---|
| a | 0.47– 0.60 ppm (m, 8H) |
| b | 0.93 ppm (t, 9H, J = 8.1 Hz) |
| c | 1.25 ppm (s, 15H) |
| d | 1.53– 1.60 ppm (m, 2H) |

$^1$H-NMR (CDCl$_3$)

a 0.47–0.60 ppm (m, 8H)

b 0.93 ppm (t, 9H, J=8.1 Hz)

c 1.25 ppm (s, 15H)

d 1.53–1.60 ppm (m, 2H)

IR spectrometric analysis

IR (neat)

1768 cm$^{-1}$ (C=O expansion and contraction)

1093 cm$^{-1}$ (C—O expansion and contraction)

848 cm$^{-1}$ (O—O expansion and contraction)

Incidentally, the measurements of the amount of active oxygen (concentration of active oxygen) and the 10-hour half-life period temperature were effected in accordance with the following methods.

Method for measuring the amount of active oxygen (iodometry method):

This method was effected according to the method described in "Organic peroxides, and their chemistry and industrial applications" edited by Study group for organic peroxides (published by Kagaku Kogyo Co. in 1952). Specifically, a triangular flask having an internal volume of 300 mL with ground stopper was charged with 30 mL of benzene. After carbon dioxide was introduced into the flask for 30 seconds (flow rate: about 2.5 L/min.), a sample (1.5–1.8 meq) was accurately weighed and then charged therein. Subsequently, 2 mL of an aqueous saturated solution of sodium iodide was added and 70 mL of an aqueous solution containing ferric chloride and acetic acid (FeCl$_3$.6H$_2$O: 0.0002 weight %) was then added. The content was well mixed and then left to stand in the dark for 15 minutes. After 80 mL of pure water was added, titration was effected with 0.1 N-solution of sodium thiosulfate until the content became colorless while a blank test was simultaneously conducted under the same conditions as above, whereby the amount of active oxygen in the sample was determined.

Method for measuring the 10-hour half-life period temperature:

A benzene solution of a sample containing 0.1 mole of the sample per liter of benzene was prepared and sealed in a glass tube of which atmosphere had been replaced with nitrogen. Then, the glass tube was placed in a constant temperature bath set at a prescribed temperature to thermally decompose the sample present in the glass tube, and changes with the lapse of time in the concentration of any residual sample undecomposed was measured from said method for measuring the amount of active oxygen to calculate the decomposition rate constant (K) at the prescribed temperature according to the following thermal decomposition equation.

Thermal decomposition equation:

$$I = I_0 \exp(-K \cdot t)$$

wherein I=½ I$_0$, in which I is the concentration of a sample and I$_0$ is the initial concentration of the sample, K is the decomposition rate constant at the prescribed temperatures (in this Example, measured at four different temperatures), and t is time (10 hours).

Next, by Arrhenius-plotting the obtained K values in a coordinate, in which the axis of ordinate is ln K and the axis of abscissa is 1/(R·T), the activated energy (Ea) of the sample was determined from the inclination of the plotted line to calculate the frequency factor (A) from its y intercept. Then, these Ea and A were substituted into the following decomposition rate equation to calculate the 10-hour half-life period temperature (T).

Decomposition rate equation:

$$\ln(K) = \ln(A) - Ea/(R \cdot T)$$

The measurements of the amounts of active oxygen and the 10-hour half-life period temperatures as mentioned below were conducted in the same manner as above.

Example 2

Production of 1,1-dimethyl-3-(triethylsilyl)propyl peroxyneodecanoate

An intended compound was obtained in the same manner as Example 1, except that in (3) of Example 1, the amount of 1,1-dimethyl-3-(triethylsilyl)propyl-1-hydroperoxide used was changed from 13.4 g (0.061 mole) to 14.2 g (0.065 mole), and 8.4 g (0.07 mole) of pivalic acid chloride was replaced with 13.9 g (0.073 mole) of neodecanoic acid chloride. The intended compound thus obtained was analyzed by the iodometry method. As a result, the yield was 14.9 g (0.040 mole) and 61.5% (mole yield based on acyl fluoride). Further, the obtained compound was analyzed for mass spectrum, IR spectrum and NMR spectrum. As a result, it was confirmed that the compound was 1,1-dimethyl-3-(triethylsilyl)propyl peroxyneodecanoate. The 10-hour half-life period temperature of the obtained compound in a benzene solution containing 0.1 mole of the compound per liter of benzene was 42.8° C. and the amount of active oxygen was 4.29%. The results of the analyses are shown below.

Mass spectrometric analysis
Exact Mass: m/z 372.6642
C$_{21}$O$_3$SiH$_{44}$ 372.6641 (calculated)
NMR spectrometric analysis

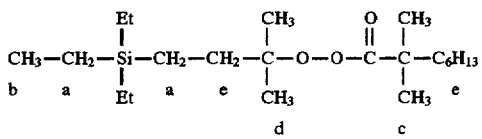

wherein Et is an ethyl group.

| $^1$H-NMR (CDCl$_3$) | |
|---|---|
| a | 0.43–0.58 ppm(m, 8H) |
| b | 0.92 ppm(t, 9H, J = 8.1 Hz) |
| c | 1.21 ppm(s, 6H) |
| d | 1.27 ppm(s, 6H) |
| e | 0.72–1.66 ppm(m, 15H) |

IR spectrometric analysis
IR (neat)
1766 cm$^{-1}$ (C=O expansion and contraction)
1099 cm$^{-1}$ (C—O expansion and contraction)
850 cm$^{-1}$ (O—O expansion and contraction)

Example 3

Production of 1,1-dimethyl-3-(triethylsilyl)propyl peroxyneotridecanoate

An intended compound was obtained in the same manner as Example 1, except that in (3) of Example 1, the amount of 1,1-dimethyl-3-(triethylsilyl)propyl-1-hydroperoxide used was changed from 13.4 g (0.061 mole) to 15.7 g (0.072 mole), and 8.4 g (0.07 mole) of pivalic acid chloride was replaced with 18.9 g (0.081 mole) of neotridecanoic acid chloride. The intended compound thus obtained was analyzed by the iodometry method. As a result, the yield was 16.6 g (0.040 mole) and 56.1% (mole yield based on acyl fluoride). Further, the obtained compound was analyzed for mass spectrum, IR spectrum and NMR spectrum. As a result, it was confirmed that the compound was 1,1-dimethyl-3-(triethylsilyl)propyl peroxyneotridecanoate. The 10-hour half-life period temperature of the obtained compound in a benzene solution containing 0.1 mole of the compound per liter of benzene was 39.5° C. and the amount of active oxygen was 3.86%. The results of the analyses are shown below.

Mass spectrometric analysis
Exact Mass: m/z 414.7449
C$_{21}$O$_3$SiH$_{44}$ 414.7447 (calculated)
NMR spectrometric analysis

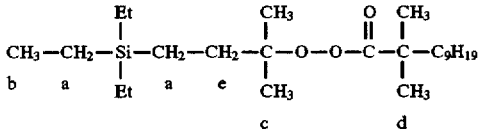

wherein Et is an ethyl group.

| $^1$H-NMR (CDCl$_3$) | |
|---|---|
| a | 0.41–0.60 ppm(m, 8H) |
| b | 0.95 ppm(t, 9H, J = 8.1 Hz) |
| c | 1.25 ppm(s, 6H) |

| | |
|---|---|
| d | 1.22 ppm(s, 6H) |
| e | 0.70–1.65 ppm(s, 21H) |

IR spectrometric analysis
IR (neat)
1770 cm$^{-1}$ (C=O expansion and contraction)
1095 cm$^{-1}$ (C—O expansion and contraction)
851 cm$^{-1}$ (O—O expansion and contraction)

Example 4

Production of 1,1-dimethyl-3-(tert-butyldimethylsilyl) propyl peroxyneoheptanoate 1,1-dimethyl-3-(tert-butyldimethyllsilyl)propyl-1-hydroperoxide was obtained in the same procedure as (1) and (2) of Example 1, except that in (1) and (2) of Example 1, 109.6 g (0.943 mole) of triethylsilane was replaced with 106 g (0.917 mole) of tert-butyldimethylsilane. An intended compound was obtained in the same manner as Example 1, except that in (3) of Example 1, 13.4 g (0.061 mole) of 1,1-dimethyl-3-(triethylsilyl)propyl-1-hydroperoxide was replaced with 14.0 g (0.064 mole) of the aforementioned 1,1-dimethyl-3-(tert-butyldimethyllsilyl)propyl-1-hydroperoxide and further 8.4 g (0.07 mole) of pivalic acid chloride was replaced with 10.7 g (0.072 mole) of neoheptanoic acid chloride. The yield of the intended compound thus obtained was 72.3% (mole yield based on acyl fluoride). Further, the obtained compound was analyzed for mass spectrum, IR spectrum and NMR spectrum. As a result, it was confirmed that the compound was 1,1-dimethyl-3-(tert-butyldimethylsilyl)propyl peroxyneoheptanoate. The 10-hour half-life period temperature of the obtained compound in a benzene solution containing 0.1 mole of the compound per liter of benzene was 46.7° C. and the amount of active oxygen was 4.84%. The results of the analyses are shown below.

Mass spectrometric analysis
Exact Mass: m/z 330.5834
$C_{18}O_3SiH_{38}$ 330.5834 (calculated)
NMR spectrometric analysis NMR spectrometric analysis $$H_3C-\underset{\underset{CH_3}{|}}{\overset{\overset{CH_3}{|}}{C}}-\underset{\underset{CH_3\ b}{|}}{\overset{\overset{CH_3}{|}}{Si}}-CH_2-CH_2-\underset{\underset{CH_3}{|}}{\overset{\overset{CH_3}{|}}{C}}-O-O-\overset{\overset{O}{\|}}{C}-\underset{\underset{CH_3}{|}}{\overset{\overset{CH_3}{|}}{C}}-C_3H_7$$
c   a        f     e        d $^1$H-NMR (CDCl$_3$)

| | |
|---|---|
| a | 0.08 ppm (s, 6H) |
| b | 0.61– 0.72 ppm (m, 2H) |
| c | 1.02 ppm (s, 9H) |
| d | 1.19 ppm (s, 6H) |
| e | 1.28 ppm (s, 6H) |
| f | 0.82– 0.63 ppm (m, 9H) |

IR spectrometric analysis
IR (neat)
1769 cm$^{-1}$ (C=O expansion and contraction)
1093 cm$^{-1}$ (C—O expansion and contraction)
852 cm$^{-1}$ (O—O expansion and contraction)

Next, there are shown Application Examples using the silicon-containing peroxyesters obtained in the present Examples as polymerization initiators for vinyl chloride monomers, and their Comparative Examples.

Application Example 1

There was used a polymerization vessel made of stainless steel having an internal volume of 2 L with an internal-temperature-adjusting coil. Into the polymerization vessel, 1,300 g of deionized water, 0.36 g of a partially saponified water-soluble polyvinyl alcohol and 0.24 g of water-soluble cellulose ether were charged. After the inside of the polymerization vessel was evacuated until the internal pressure of the polymerization vessel reached 50 mmHg (absolute pressure), 400 g of vinyl chloride was charged therein. Then, heated water was passed through the coil, while stirring the content of the polymerization vessel, to raise the internal temperature of the polymerization vessel until the internal temperature reached 57° C. (polymerization temperature). At the time when the internal pressure (a pressure during polymerization) of the polymerization vessel reached the pressure given in Table 1, a 25 weight % isoparaffin solution of 1,1-dimethyl-3-(tert-butyldimethylsilyl)propyl peroxyneoheptanoate (in Table 1, abbreviated to TBSNH) poured into the polymerization vessel in the amount added as given in Table 1 by means of an injector to start polymerization. Simultaneously with the start of polymerization, cooling water was passed through the coil to continue polymerization while maintaining the internal temperature to 57° C. (polymerization temperature). At the time when the internal pressure of the polymerization vessel dropped to the pressure given in Table 1 (in Table 1, represented as internal pressure (kgf/cm$^2$) of polymerization vessel when polymerization was stopped), 0.31 g of a 20 weight % methanol solution of bisphenol A was poured into the polymerization vessel by means of an injector to stop polymerization. Then, after gas (monomer) within the polymerization vessel was exhausted, vinyl chloride polymer was taken out as slurry from the polymerization vessel. In Table 1, there are given the polymerization temperature (° C.), the internal pressure of the polymerization vessel immediately before the internal pressure of the polymerization vessel began to drop after the start of polymerization [in Table 1, represented as polymerization vessel internal pressure (kgf/cm$^2$) before pressure drop], the rate of the pressure drop ranging from the internal pressure of the polymerization vessel at the time when the internal pressure of the polymerization vessel began to drop to the internal pressure of the polymerization vessel at the time when polymerization was stopped [in Table 1, represented as rate of pressure drop (kgf/cm$^2$/hr)], the internal pressure of the polymerization vessel when polymerization was stopped [in Table 1, represented as polymerization vessel internal pressure (kgf/cm$^2$) when polymerization was stopped], the period from the start of polymerization (the start means the time when the polymerization initiator was charged) until the internal pressure of the polymerization vessel began to drop [in Table 1, represented as time (minute) until pressure drop], the period from the beginning of the pressure drop until the stop of polymerization, the period from the start of polymerization until the stop of polymerization, [in Table 1, represented as total polymerization time (minute)], and the yield (%) of the obtained vinyl chloride polymer.

Subsequently, an evaluation test for initial discoloration with regard to the obtained vinyl chloride polymer was effected in accordance with the following methods. The results are shown in Table 1.

Evaluation test for initial discoloration

To 100 parts by weight of the vinyl chloride polymer, there were compounded 1 part by weight of tin laurate, 0.5 part by weight of a cadmium-based stabilizer and 50 parts by weight of DOP. After blending them at 150° C. for 5 minutes using a two-roll mill, the resulting composition was stretched into a sheet having a thickness of 0.8 mm. The sheet was cut into pieces which were placed in layers in a frame of 4×4×1.5 cm. The layers was then heat-pressed at 150° C. under 65–70 kgf/cm² to form a specimen for measurement. The specimen for measurement was determined using a photoelectric color meter (manufactured by Nihondenshoku Kogyo Co. Ltd.) for luminosity index L in the Hunter's color difference equation described in JIS Z 8730 (1980), and measured for a and b values to evaluate according to the following criterion.

Evaluation criterion:
Evaluation rank ⊚ . . . excellent
Evaluation rank ○ . . . good
Evaluation rank Δ . . . slightly poor
Evaluation rank X . . . poor Comparative Example 1

A vinyl chloride polymer was obtained in the same manner as Application Example 1, except that in Application Example 1, a 25 weight % isoparaffin solution of tert-butyl peroxyneodecanoate (in Table 1, abbreviated to TBND) in place of 1,1-dimethyl-3-(tert-butyldimethylsilyl)propyl peroxyneoheptanoate was poured into the polymerization vessel in the amount added as given in Table 1 by means of an injector to start polymerization and to effect polymerization under the conditions as given in Table 1. The yield (%) of the vinyl chloride polymer and the results of the evaluation test for initial discoloration, which test was effected in the same manner as in Application Example 1, were shown in Table 1. Also, the 10-hour half-life period temperature of the aforementioned TBND in a benzene solution containing 0.1 mole of TBND per liter of benzene was listed together in Table 1.

Comparative Example 2

A vinyl chloride polymer was obtained in the same manner as Application Example 1, except that in Application Example 1, a 25 weight % isoparaffin solution of di-2-ethylhexyl peroxydicarbonate (in Table 1, abbreviated to EHP) in place of 1,1-dimethyl-3-(tert-butyldimethylsilyl) propyl peroxyneoheptanoate was poured into the polymerization vessel in the amount added as given in Table 1 by means of an injector to start polymerization and to effect polymerization under the conditions as given in Table 1. The yield (%) of the vinyl chloride polymer and the results of the evaluation test for initial discoloration, which test was effected in the same manner as in Application Example 1, were shown in Table 1. Also, the 10-hour half-life period temperature of the aforementioned EHP in a benzene solution containing 0.1 mole of EHP per liter of benzene was listed together in Table 1.

Comparative Example 3

A vinyl chloride polymer was obtained in the same manner as Application Example 1, except that in Application Example 1, a 25 weight % isoparaffin solution of 3,5,5-trimethylhexanoyl peroxide (in Table 1, abbreviated to TMHP) in place of 1,1-dimethyl-3-(tert-butyldimethylsilyl) propyl peroxyneoheptanoate was poured into the polymerization vessel in the amount added as given in Table 1 by means of an injector to start polymerization and to effect polymerization under the conditions as given in Table 1. The yield (%) of the vinyl chloride polymer and the results of the evaluation test for initial discoloration, which test was effected in the same manner as in Application Example 1, were shown in Table 1. Also, the 10-hour half-life period temperature of the aforementioned TMHP in a benzene solution containing 0.1 mole of TMHP per liter of benzene was listed together in Table 1.

TABLE 1

| | | | Application Example 1 | Comparative Example 1 | Comparative Example 2 | Comparative Example 3 |
|---|---|---|---|---|---|---|
| Polymerization initiator | Kind | | TBSNH | TBND | EHP | TMHP |
| | 10-hour half-life period temperature (°C.) *1 | | 46.7 | 46.5 | 43.5 | 59.5 |
| | Amount added | wt. % *2 | 0.152 | 0.113 | 0.159 | 0.145 |
| | | mole % *3 | 4.60 × 10⁻⁴ | 4.62 × 10⁻⁴ | 4.60 × 10⁻⁴ | 4.62 × 10⁻⁴ |
| Polymerization temperature (°C.) | | | 57.0 | 57.0 | 57.0 | 57.0 |
| Polymerization vessel internal pressure before pressure drop (kgf/cm²) | | | 8.5 | 8.5 | 8.5 | 8.5 |
| Rate of pressure drop (kgf/cm²/hr) | | | 5.0 | 2.2 | 4.4 | 3.2 |
| Polymerization vessel internal pressure when polymerization was stopped (kgf/cm²) | | | 4.9 | 4.9 | 4.9 | 4.9 |
| Time until pressure drop (min.) | | | 119 | 133 | 112 | 328 |
| Time from beginning of pressure drop until stop of polymerization (min.) | | | 38 | 98 | 48 | 67 |
| Total polymerization time (min.) | | | 157 | 231 | 160 | 395 |
| Yield (%) | | | 89.3 | 89.2 | 89.3 | 89.1 |
| Initial discoloration | L value | | 70.0 | 69.8 | 67.5 | 69.1 |
| | a value | | −1.1 | −1.4 | −1.0 | −1.2 |
| | b value | | 11.7 | 12.1 | 15.9 | 12.8 |
| | Evaluation | | ⊚ | ○ | x | Δ |

15

In Table 1, *1 denotes the 10-hour half-life period temperature of a compound, which is measured, in a benzene solution containing 0.1 mole of the compound per liter of benzene. *2 and *3 denote % based on vinyl chloride monomer.

Application Example 2

A vinyl chloride polymer was obtained in the same manner as Application Example 1, except that in Application Example 1, the polymerization temperature was changed from 57° C. to 60° C. and a 25 weight % isoparaffin solution of 1,1-dimethyl-3-(triethylsilyl)propyl peroxypivalate (in Table 2, abbreviated to TESPV) in place of 1,1-dimethyl-3-(tert-butyldimethylsilyl)propyl peroxyneoheptanoate was poured into the polymerization vessel in the amount added as given in Table 2 by means of an injector to start polymerization and to effect polymerization under the conditions as given in Table 2. The yield (%) of the vinyl chloride polymer and the results of the evaluation test for initial discoloration, which test was effected in the same manner as in Application Example 1, were shown in Table 2. Also, the 10-hour half-life period temperature of the aforementioned TESPV in a benzene solution containing 0.1 mole of TESPV per liter of benzene was listed together in Table 1.

Comparative Example 4

A vinyl chloride polymer was obtained in the same manner as Application Example 2, except that in Application Example 2, a 25 weight % isoparaffin solution of tert-butyl peroxyneodecanoate (in Table 2, abbreviated to TBND) in place of 1,1-dimethyl-3-(triethylsilyl)propyl peroxypivalate was poured into the polymerization vessel in the amount added as given in Table 2 by means of an injector to start polymerization and to effect polymerization under the conditions as given in Table 2. The yield (%) of the vinyl chloride polymer and the results of the evaluation test for initial discoloration, which test was effected in the same manner as in Application Example 2, were shown in Table 2. Also, the 10-hour half-life period temperature of the aforementioned TBND in a benzene solution containing 0.1 mole of TBND per liter of benzene was listed together in Table 2.

Comparative Example 5

A vinyl chloride polymer was obtained in the same manner as Application Example 2, except that in Application Example 2, a 25 weight % isoparaffin solution of 3,5,5-trimethylhexanoyl peroxide (in Table 2, abbreviated to TMHP) in place of 1,1-dimethyl-3-(triethylsilyl)propyl peroxypivalate was poured into the polymerization vessel in the amount added as given in Table 2 by means of an injector to start polymerization and to effect polymerization under the conditions as given in Table 2. The yield (%) of the vinyl chloride polymer and the results of the evaluation test for initial discoloration, which test was effected in the same manner as in Application Example 2, were shown in Table 2. Also, the 10-hour half-life period temperature of the aforementioned TMHP in a benzene solution containing 0.1 mole of TMHP per liter of benzene was listed together in Table 2.

TABLE 2

|  |  | Application Example 2 | Comparative Example 4 | Comparative Example 5 |
| --- | --- | --- | --- | --- |
| Polymerization initiator | Kind | TESPV | TBND | TMHP |
|  | 10-hour half-life period temperature (°C.) *1 | 49.4 | 46.5 | 59.5 |
|  | Amount added wt. % *2 | 0.111 | 0.090 | 0.116 |
|  | mole % *3 | $3.67 \times 10^{-4}$ | $3.68 \times 10^{-4}$ | $3.69 \times 10^{-4}$ |
| Polymerization temperature (°C.) |  | 60.0 | 60.0 | 60.0 |
| Polymerization vessel internal pressure before pressure drop (kgf/cm$^2$) |  | 9.3 | 9.3 | 9.3 |
| Rate of pressure drop (kgf/cm$^2$/hr) |  | 5.8 | 2.7 | 3.3 |
| Polymerization vessel internal pressure when polymerization was stopped (kgf/cm$^2$) |  | 6.5 | 6.5 | 6.5 |
| Time until pressure drop (min.) |  | 152 | 217 | 341 |
| Time from beginning of pressure drop until stop of polymerization (min.) |  | 29 | 62 | 51 |
| Total polymerization time (min.) |  | 181 | 279 | 392 |
| Yield (%) |  | 86.3 | 86.2 | 86.1 |
| Initial discoloration | L value | 70.1 | 70.2 | 69.6 |
|  | a value | −1.3 | −1.1 | −1.2 |
|  | b Value | 11.1 | 11.2 | 12.6 |
|  | Evaluation | ⊚ | ⊚ | Δ |

In Table 2, *1 denotes the 10-hour half-life period temperature of a compound, which is measured, in a benzene solution containing 0.1 mole of the compound per liter of benzene. *2 and *3 denote % based on vinyl chloride monomer.

Application Example 3

A vinyl chloride polymer was obtained in the same manner as Application Example 1, except that in Application Example 1, the polymerization temperature was changed from 57° C. to 54° C. and a 25 weight % isoparaffin solution of 1,1-dimethyl-3-(triethylsilyl)propyl peroxyneodecanoate (in Table 3, abbreviated to TESND) in place of 1,1-dimethyl-3-(tert-butyldimethylsilyl)propyl peroxyneoheptanoate was poured into the polymerization vessel in the amount added as given in Table 3 by means of an injector to start polymerization and to effect polymerization under the conditions as given in Table 3. The yield (%) of the vinyl chloride polymer and the results of the evaluation test for initial discoloration, which test was effected in the same manner as in Application Example 1, were shown in Table 3. Also, the 10-hour half-life period temperature of the aforementioned TESND in a benzene solution containing 0.1 mole of TESND per liter of benzene was listed together in Table 3.

Comparative Example 6

A vinyl chloride polymer was obtained in the same manner as Application Example 3, except that in Application Example 3, a 25 weight % isoparaffin solution of di-2-ethylhexyl peroxydicarbonate (in Table 3, abbreviated to EHP) in place of 1,1-dimethyl-3-(triethylsilyl)propyl peroxyneodecanoate was poured into the polymerization vessel in the amount added as given in Table 3 by means of an injector to start polymerization and to effect polymerization under the conditions as given in Table 3. The yield (%) of the vinyl chloride polymer and the results of the evaluation test for initial discoloration, which test was effected in the same manner as in Application Example 3, were shown in Table 3. Also, the 10-hour half-life period temperature of the aforementioned EHP in a benzene solution containing 0.1 mole of EHP per liter of benzene was listed together in Table 3.

Comparative Example 7

A vinyl chloride polymer was obtained in the same manner as Application Example 3, except that in Application Example 3, a 25 weight % isoparaffin solution of cumyl peroxyneodecanoate (in Table 3, abbreviated to CND) in place of 1,1-dimethyl-3-(triethylsilyl)propyl peroxyneodecanoate was poured into the polymerization vessel in the amount added as given in Table 3 by means of an injector to start polymerization and to effect polymerization under the conditions as given in Table 3. The yield (%) of the vinyl chloride polymer and the results of the evaluation test for initial discoloration, which test was effected in the same manner as in Application Example 3, were shown in Table 3. Also, the 10-hour half-life period temperature of the aforementioned CND in a benzene solution containing 0.1 mole of CND per liter of benzene was listed together in Table 3.

Application Example 4

A vinyl chloride polymer was obtained in the same manner as Application Example 1, except that in Application Example 1, the polymerization temperature was changed from 57° C. to 51° C. and a 25 weight % isoparaffin solution of 1,1-dimethyl-3-(triethylsilyl)propyl peroxyneotridecanoate (in Table 3, abbreviated to TESTD) in place of 1,1-dimethyl-3-(tert-butyldimethylsilyl)propyl peroxyneoheptanoate was poured into the polymerization vessel in the amount added as given in Table 3 by means of an injector to start polymerization and to effect polymerization under the conditions as given in Table 3. The yield (%) of the vinyl chloride polymer and the results of the evaluation test for initial discoloration, which test was effected in the same manner as in Application Example 1, were shown in Table 3. Also, the 10-hour half-life period temperature of the aforementioned TESTD in a benzene solution containing 0.1 mole of TESTD per liter of benzene was listed together in Table 3.

Comparative Example 8

A vinyl chloride polymer was obtained in the same manner as Application Example 4, except that in Application Example 4, a 25 weight % isoparaffin solution of cumyl peroxyneodecanoate (in Table 3, abbreviated to CND) in place of 1,1-dimethyl-3-(triethylsilyl)propyl peroxyneotridecanoate was poured into the polymerization vessel in the amount added as given in Table 3 by means of an injector to start polymerization and to effect polymerization under the conditions as given in Table 3. The yield (%) of the vinyl chloride polymer and the results of the evaluation test for initial discoloration, which test was effected in the same manner as in Application Example 4, were shown in Table 3. Also, the 10-hour half-life period temperature of the aforementioned CND in a benzene solution containing 0.1 mole of CND per liter of benzene was listed together in Table 3.

TABLE 3

| | | Application Example 3 | Comparative Example 6 | Comparative Example 7 | Application Example 4 | Comparative Example 8 |
|---|---|---|---|---|---|---|
| Polymerization initiator | Kind | TESND | EHP | CND | TESND | CND |
| | 10-hour half-life period temperature (°C.) *1 | 42.8 | 43.5 | 36.6 | 39.5 | 36.6 |
| | amount added wt. % *2 | 0.161 | 0.150 | 0.132 | 0.203 | 0.150 |
| | mole % *3 | $4.32 \times 10^{-4}$ | $4.32 \times 10^{-4}$ | $4.31 \times 10^{-4}$ | $4.90 \times 10^{-4}$ | $4.90 \times 10^{-4}$ |
| Polymerization temperature (°C.) | | 54.0 | 54.0 | 54.0 | 51.0 | 51.0 |
| Polymerization vessel internal pressure before pressure drop (kgf/cm$^2$) | | 7.9 | 7.9 | 7.9 | 7.2 | 7.2 |
| Rate of pressure drop (kgf/cm$^2$/hr) | | 6.6 | 5.1 | 1.8 | 4.7 | 1.5 |
| Polymerization vessel internal pressure when polymerization was stopped (kgf/cm$^2$) | | 4.5 | 4.5 | 5.1 | 5.0 | 5.0 |
| Time until pressure drop (min.) | | 130 | 137 | 124 | 131 | 14.7 |
| Time from beginning of pressure drop until stop of polymerization (min.) | | 31 | 40 | 93 | 28 | 88 |
| Total polymerization time (min.) | | 161 | 177 | 217 | 159 | 235 |
| Yield (%) | | 89.2 | 89.2 | 87.3 | 86.1 | 86.1 |
| Initial discoloration | L value | 69.9 | 67.1 | 70.0 | 69.7 | 69.6 |
| | a value | −1.1 | −1.0 | −1.1 | −1.2 | −1.1 |
| | b value | 11.8 | 16.2 | 11.5 | 12.0 | 12.1 |
| | Evaluation | ⊚ | x | ⊚ | o | o |

In Table 3, *1 denotes the 10-hour half-life period temperature of a compound, which is measured, in a benzene solution containing 0.1 mole of the compound per liter of benzene. *2 and *3 denote % based on vinyl chloride monomer.

What is claimed is:

1. A silicon-containing peroxyester compound represented by the general formula (1):

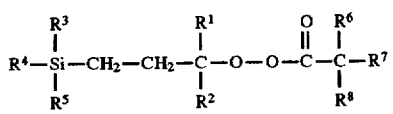

(1)

wherein $R^1$ and $R^2$ are the same or different and are a straight-chain alkyl group having 1 to 6 carbon atoms or a branched chain alkyl group having 3 to 6 carbon atoms; $R^3$, $R^4$ and $R^5$ are the same or different and are a straight-chain alkyl group having 1 to 6 carbon atoms, a branched chain alkyl group having 3 to 6 carbon atoms or an aryl group having 6 to 9 carbon atoms; and $R^6$, $R^7$ and $R^8$ are the same or different and are a straight-chain alkyl group having 1 to 9 carbon atoms, provided that the total number of the carbon atoms of $R^6$, $R^7$ and $R^8$ is 11 or less.

2. The silicon-containing peroxyester compound claimed in claim 1, comprising a compound selected from the group consisting of 1,1-dimethyl-3-(triethylsilyl)propyl peroxypivalate, 1,1-dimethyl-3-(triethylsilyl)propyl peroxyneoheptanoate, 1,1-dimethyl-3-(triethylsilyl)propyl peroxyneodecanoate, 1,1-dimethyl-3-(phenyldimethylsilyl) propyl peroxypivalate, 1,1-dimethyl-3-(phenyldimethylsilyl)propyl peroxyneoheptanoate, 1,1-dimethyl-3-(phenyldimethylsilyl)propyl peroxyneodecanoate, 1,1-dimethyl-3-(tert-butyldimethylsilyl)propyl peroxypivalate, 1,1-dimethyl-3-(tert-butyldimethylsilyl)propyl peroxyneoheptanoate, 1,1-dimethyl-3-(tert-butyldimethylsilyl)propyl peroxyneodecanoate, 1-ethyl-1-methyl-3-(trietylsilyl)propyl peroxypivalate, 1-ethyl-1-methyl-3-(trietylsilyl)propyl peroxyneoheptanoate, 1-ethyl-1-methyl-3-(trietylsilyl) propyl peroxyneodecanoate, 1,1-dimethyl-3-(triethylsilyl)propyl peroxyneotridecanoate, 1,1-dimethyl-3-(phenyldimethylsilyl)propyl peroxyneotridecanoate, 1,1-dimethyl-3-(tert-butyldimethylsilyl)propyl peroxyneotridecanoate, and 1-ethyl-1-methyl-3-(triethylsilyl)propyl peroxyneotridecanoate.

* * * * *